(12) United States Patent
Bergeron et al.

(10) Patent No.: US 8,460,720 B2
(45) Date of Patent: Jun. 11, 2013

(54) HOPS-BASED DEODORANT

(75) Inventors: Chantal Bergeron, Kennebunkport, ME (US); Stefan Gafner, Kennebunkport, ME (US); Jennifer L. Lafrance, Biddeford, ME (US)

(73) Assignee: Tom's of Maine, Inc., Kennebunk, MA (US)

( * ) Notice: Subject to any disclaimer, the term of this patent is extended or adjusted under 35 U.S.C. 154(b) by 599 days.

(21) Appl. No.: 12/243,329

(22) Filed: Oct. 1, 2008

(65) Prior Publication Data

US 2009/0098075 A1    Apr. 16, 2009

Related U.S. Application Data

(60) Provisional application No. 60/997,118, filed on Oct. 1, 2007.

(51) Int. Cl.
*A61K 36/89* (2006.01)
*A61K 36/00* (2006.01)

(52) U.S. Cl.
USPC .......................................... 424/750; 424/776

(58) Field of Classification Search
None
See application file for complete search history.

(56) References Cited

U.S. PATENT DOCUMENTS

| | | | |
|---|---|---|---|
| 4,101,409 A | 7/1978 | Austin | |
| 4,170,638 A | 10/1979 | Owades | |
| 5,714,447 A | 2/1998 | Jones et al. | |
| 6,001,342 A | 12/1999 | Forestier et al. | |
| 6,475,537 B1 * | 11/2002 | King et al. | 424/778 |
| 6,780,825 B2 * | 8/2004 | Piterski et al. | 510/124 |
| 2003/0017122 A1 * | 1/2003 | Vromen | 424/59 |
| 2003/0228369 A1 * | 12/2003 | Kuhrts | 424/489 |
| 2007/0036705 A1 * | 2/2007 | Butts et al. | 423/335 |

FOREIGN PATENT DOCUMENTS

DE    10205297 A1 *  8/2003

OTHER PUBLICATIONS

ASTM Committee E-18: Standard practice for the sensory evaluation of axillary deodorancy. ASTM Standards, vol. 15.07, designation: E 1207-87, 1988; 51-66.
Dumas et al., 2009, "Deodorant effects of a supercritical hops extract: antibacterial activity against Corynebacterium xerosis and Staphylococcus epidermidis and efficacy testing of a hops/zinc ricinoleate stick in humans through the sensory evaluation of axillary deodorancy," J. Cosmetic Dermatology 8(3):197-204.
Gower et al., 1997, "Capillary gas chromatography with chemical ionization negative ion mass spectrometry in the identification of odorous steroids formed in metabolic studies of the sulphates of androsterone, DHA and 5alpha-androst-16-en-3beta-ol with human axillary bacterial isolates," J. Steroid Biochem. Mol. Biol. 63(1-3):81-89.
Jackman et al., 1983, "Normal axillary skin microflora in various populations," Clinical Exp. Dermatol. 8:259-268.
Jorgensen et al., 1993, "Methods for Dilution Antimicrobial Susceptibility Tests for Bacteria That Grow Aerobically—Third Edition; Approved Standard," National Committee for Clinical Laboratory Standards, Document M7-A3, NCCLS, Villanova, PA 13(25):1-32.
Lanzalaco et al., 2004, "Clinical Effect of a Three-Day Application of a Commercial Deodorant on Axilla Malodor Intensity, Microbial Population Level, and Longevity of Fragrance Expression," J. Amer. Acad. Dermatol. 50:P73, Abstract.
Lewis et al., 1949, "Lupulon and Humulon — Antibiotic Constituents of Hops," J. Clin. Invest. 28:916-919.
Leyden et al., 1981, "The microbiology of the human axilla and its relationship to axillary odor," J. Invest. Dermatol. 77(5):413-416.
Murphy et al., 1991, "Analysis of Antiperspirant Efficacy Test Results," J. Soc. Cosmetic Chem. 42:167-197.
Natsch et al., 2003, "A specific bacterial aminoacylase cleaves odorant precursors secreted in the human axilla," J. Biol. Chem. 278(8):5718-5727.
Natsch et al., 2004, "Identification of odoriferous sulfanylalkanols in human axilla secretions and their formation through cleavage of cysteine precursors by a C-S lyase isolated from axilla bacteria," Chem. Biodiv. 1(7):1058-1072.
Sakamoto et al., 2003, "Beer spoilage bacteria and hop resistance," Int. J. Food Microbiol. 89(2-3):105-124.
Schmalreck et al., 1975, "Structural features determining the antibiotic potencies of natural and synthetic hop bitter resins, their precursors and derivatives," Can. J. Microbiol. 21(2):205-212.
Simpson, 1993, "Cambridge Prize Lecture. Studies on the Sensitivity of Lactic Acid Bacteria to Hop Bitter Acids," J. Inst. Brew. 99:405-411.
Takenaka et al., 2004, "Analysis of Isovaleric Acid Generation by Skin Resident Microorganisms in Body Malodors, and the Inhibitory Effect of Sophora flavescens Extract," J. Jpn. Cosmet. Sci. Soc. 28:177-182.
Taylor et al., 2003, "Characterization of the microflora of the human axilla," Int. J. Cosmetic Sci. 25(3):137-45.
Troccaz et al., 2004, "3-Methyl-3-sulfanylhexan-1-ol as a major descriptor for the human axilla-sweat odour profile," Chem. Biodiversity 1(7):1022-1035.
Wild et al., 1999, "Clinical evaluation of antiperspirants and deodorants," Chapter 11 in: Antiperspirants and Deodorants, Laden, ed., 2nd ed., New York, Marcel Dekker Inc. pg. 320.
Yansanjav et al., 2004, "Detection of resistance of lactic acid bacteria to a mixture of the hop analogue compounds tetrahydroiso-alpha-acids by noninvasive measurement of intracellular pH," J. Appl. Microbiol. 96(6):1324-1332.
"Zinc Ricinoleate", 2009, Wikipedia, http://en.wikipedia.org/wiki/Zinc_ricinoleate.
Lanzalaco et al., 2003, "Clinical assessment of the effects of hygiene measures on axillary malodor intensity and microbial population levels," Poster presentation, 61st Annual Meeting of the American Academy of Dermatology P320.
Rocchetta, 2003, "Topical application of commercial deodorants and antiperspirants control axillary malodor via antimicrobial activity and fragrance," Poster Presentation, 61st Annual Meeting of the American Academy of Dermatology; P331.

* cited by examiner

*Primary Examiner* — Christopher R. Tate
*Assistant Examiner* — Deborah A. Davis

(57) ABSTRACT

The present invention relates to deodorants and other body care products comprising a $CO_2$ extract of the hops plant having bacteriocide/bacteriostat properties wherein the $CO_2$ extract has a very low level of essential hops oils.

17 Claims, 4 Drawing Sheets

HOPS-BASED DEODORANT

CROSS-REFERENCE TO RELATED APPLICATION

This claims priority to U.S. Provisional Application Ser. No. 60/997,118 filed Oct. 1, 2007, the disclosure of which is incorporated herein by reference.

BACKGROUND

Deodorants are traditionally used to reduce or eliminate body odor caused by the breakdown and fermentation of secretions from apocrine sweat glands. Gram positive bacteria such as *Corynebacterium xerosis, Staphylococcus aureus* and *Staphylococcus epidermis* are primary examples of odor causing bacteria that inhabit human skin. Many commercially available deodorants help to eliminate body odor by acting as a bactericide or bacteriostat. Bactericides kill bacteria while bacteriostats inhibit the growth of bacteria.

Commercially available underarm and body care products attribute their effectiveness as antimicrobial agents by the inclusion of chemicals such as triclosan, or by using astringent agents like aluminum salts (for example, in the forms of aluminum chlorohydrate, aluminum chloride, aluminum chlorohydrate and aluminum-zirconium compounds, most notably aluminum zirconium tetrachlorohydrex gly). However, these chemicals have been inked to major health concerns.

Triclosan (5-chloro-2-(2,4-dichlorophenoxy), is a broad spectrum antibiotic. Triclosan is a chlorophenol, a class of chemicals which is suspected of causing cancer in humans. It is known to react with chlorine in water to produce chlorinated dioxins, which are listed by the Environmental Protection Agency (U.S.) as probable carcinogens in humans. Triclosan is also suspected of playing a role in a host of other medical problems including causing skin irritation and acting as an endocrine disrupter. And, while triclosan is used in more products than just deodorant, a 2002 Swedish study found high levels of triclosan in 3 out of 5 human breast milk samples. Also, according to the EPA, typical triclosan preparations are "suspected to be" contaminated with highly carcinogenic dioxins.

Aluminum has been inked to Alzheimer's disease, due to high concentrations of the metal in the brains of Alzheimer's patients. Some research has also linked aluminum in deodorants and antiperspirants to breast cancer By applying these chemicals to an area near the underarm lymph nodes, some people believe they are ensuring that the chemicals are carried through the body. Although these suspicions are controversial (for example, a 2002 study by the Fred Hutchison Cancer Center in Seattle, Wash. found no correlation between deodorant use and breast cancer while a 2003 study published in the European Journal of Cancer Prevention found a significant correlation), many people would prefer to err on the side of caution and eliminate potentially harmful compounds from their deodorants and body care products.

In the desire to eliminate harmful chemicals from deodorants and body care products, people have turned to natural ingredients. For example, hops extract has been used as an antimicrobial agent in deodorants (see, for example, U.S. Pat. No. 4,170,638 to Owades; the '638 patent). However, the compositions disclosed in the '638 patent were not without substantial problems or concerns. For example, the '638 patent is directed towards the use of organic solvents for the extraction of the hops used in the invention. This is problematic because organic solvent extracts of hops retain a high percentage of plant pigments, cuticular waxes, water and water-soluble materials which may interfere with production demands, adversely affect other product ingredients or adversely affect the end user. Solvent extracts of hops must be heated to remove the organic solvent. This process is difficult as the extract is a syrupy or pasty mass and the process can damage active constituents. Additionally, solvent extracts retain solvent residues and co-purify nitrates and pesticide residues from the hops plants. Furthermore, the chemical influence of the extraction solvents on the hop ingredients is not clear in many cases and may lead to the production of toxic compounds (see, U.S. Pat. No. 4,101,409 to Vitztham, et al.).

Therefore, what is needed is a deodorant and other body care products comprising a safer all-natural antimicrobial agent that people feel is safe to use as well as being effective for reducing or preventing body odor.

SUMMARY OF THE INVENTION

The present invention provides, in one aspect, body care products (compositions) and body and underarm deodorants (deodorant compositions) that comprise one or more all-natural antimicrobial agents.

In one embodiment, one of the antimicrobial agents of the deodorant of the present invention is a $CO_2$ extract of, for example, the plant *Humulus lupulus*, more commonly known as the hop plant, or related strains and species of the plant known in the art. The ability of a $CO_2$ extract of the hop plant to function effectively as an antimicrobial agent in a body deodorant (especially as an underarm deodorant) was unknown until the conception of the present invention. This is at least in part because a $CO_2$ extract of hops results in a different mix of extractants as compared to the prior art organic solvent hops extract. Until the conception of this invention it was also unknown how or even if the constituents of the $CO_2$ extract would effect a final deodorant product from the standpoint of, for example, product production, product stability, product application and skin feel and effectiveness as a deodorant. Additionally, it was only through empirical experimentation that the methods and compositions of the present invention were conceived and reduced to practice. There were no market pressures or other market considerations that would have led one practiced in the art to identify or develop the components of the present invention, modify the components as necessary to conceive and practice the present invention and to conceive and produce the products of present invention. It was only after the conceptual reduction to practice of the present invention that any market value was recognized.

The deodorants and body care products of the present invention are not limited by the method used to produce a $CO_2$ hops extract. Hops may be extracted with either liquid $CO_2$ or supercritical $CO_2$. Both supercritical and liquid $CO_2$ hops extracts provide a greater amount of lipophilic compounds and less of the flavonoids (or phenolic compounds) from the plant than organic solvent extracts.

In a preferred embodiment, the hops extracts of the present invention are extracted in a two-step process. The two-step process of the present invention, explained in greater detail below, produces what is herein called a flavor-reduced extract. The first step produces an intermediate extract (called herein a "total extract") wherein the extract comprises essential oils and hops acids. The second step of the process produces a final extract (herein called a "flavor-reduced extract") that is very low in essential oils. In one embodiment, the extract comprises less than about 5% essential oils. In a preferred embodiment, the extract comprises less than about 2% essential oils.

The deodorant and body care products of the present invention may also comprise other deodorancy ingredients in addition to the $CO_2$ hops extract. For example, in one embodiment, it is contemplated that the deodorant of the present invention also comprises one or more of lemongrass oil or zinc ricinoleate, both known in the art to reduce or inhibit the production of body odor.

The deodorant and body care products of the present invention may also comprise other ingredients. For example, the deodorant of the present invention may comprise one or more ingredients for achieving and maintaining a desired consistency, one or more ingredients for giving the product a soothing skin feel, one or more antioxidants, one or more fragrances and one or more ingredients for fragrance duration or retention.

Non-limiting examples of ingredients suitable for use in achieving and maintaining desired consistency are, for example, caprylic capric triglyceride, propylene glycol, glycerin, glyceryl laurate, water and sodium stearate.

Non-limiting examples of ingredients suitable for use as soothing agents are, for example, aloe vera leaf juice and other herbal extracts and witch hazel water.

Non-limiting examples of ingredients suitable for use as antioxidants are, for example, one or more of tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract and, more preferably, ascorbic acid and salts thereof.

Non-limiting examples of ingredients suitable for use as fragrance are, for example, lemongrass oil, apricot fragrance, fir needle oil, lavandin oil and lavander oil.

Non-limiting examples of ingredients suitable for use for fragrance duration or longevity are silica shells.

In another embodiment, the deodorant of the present invention may comprise a "stick" formulation, a roll-on formulation or a spray formulation (e.g., as a pump spray), all of which the production is known in the art.

DESCRIPTION OF THE PREFERRED EMBODIMENTS

Figure 1:
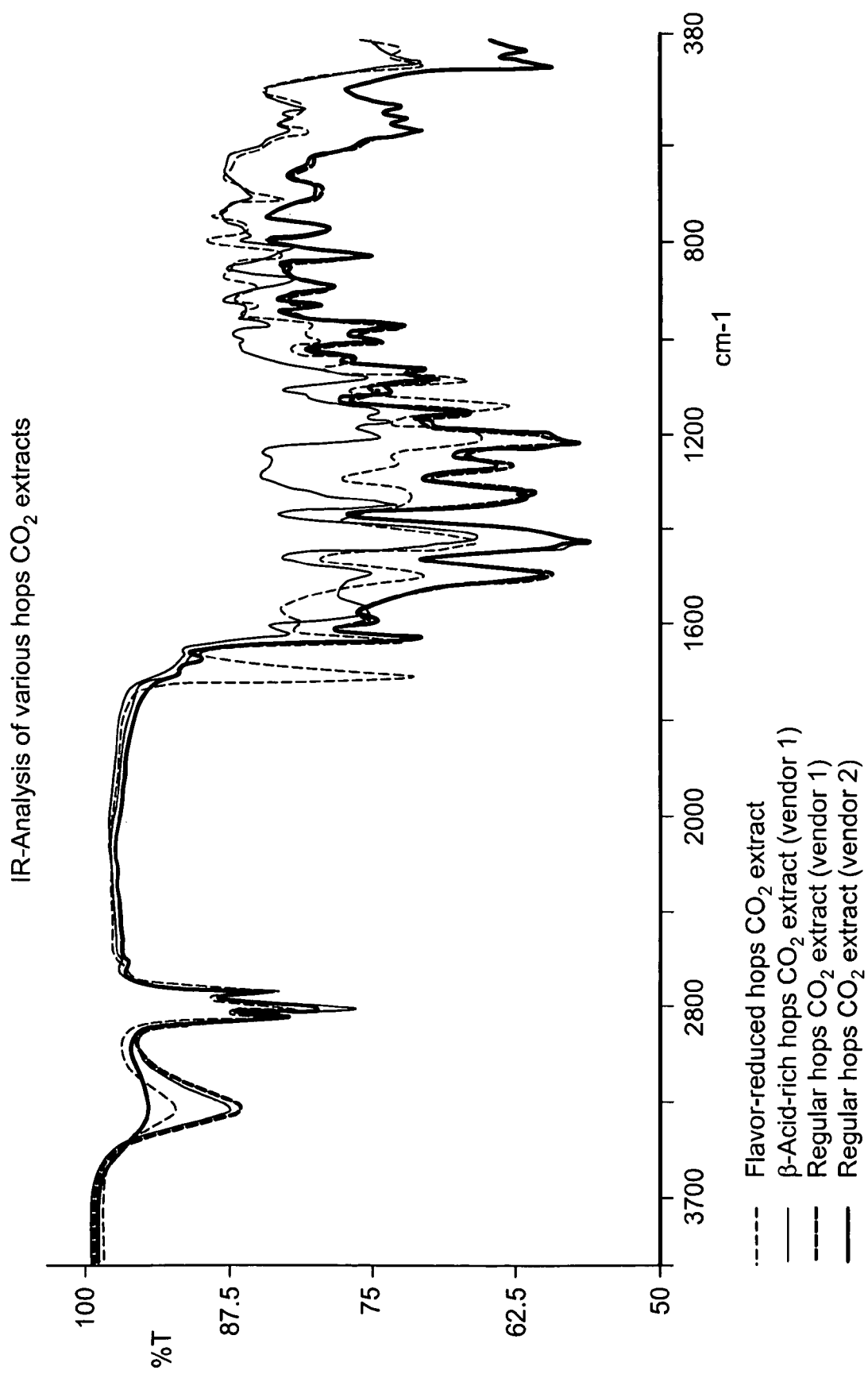
FIG. 1 shows an IR analysis (Perkin-Elmer Model Spectrum 100) of the flavor-reduced extract of the present invention as compared to three commercially produced $CO_2$ hops extracts.

The present invention relates to deodorants (especially underarm deodorants) and other body care products comprising a $CO_2$ extract of the Hops plant effective for the reduction or prevention of body odor. $CO_2$ extracts of hops plants hitherto have not been used in deodorant and body care products. Thus, it was unknown until the conceptual reduction to practice of the present invention as to whether such extracts would be effective in the reduction or prevention of body odor when used in body care and deodorant products or how such products should be formulated for effective use.

The present invention is not limited to the species or variety of hops plant used to produce the $CO_2$ extract of the present invention. The extract may be produced, for example, from one or more of the following plants: the Asian Hop *Humulus japonicus* (syn. *H. scandens*); the Yunnan Hop *Humulus yunnanensis*, and the Common Hop *Humulus lupulus*. The Common Hop has five varieties: *Humulus lupulus* var. *lupulus*, *Humulus lupulus* var. *cordifolius*, *Humulus lupulus* var. *lupuloides* (syn. *H. americanus*), *Humulus lupulus* var. *neomexicanus* and *Humulus lupulus* var. *pubescens*.

The present invention is not limited by the method used to produce the $CO_2$ hops extract. Hops may be extracted with either liquid or supercritical $CO_2$. Both supercritical and liquid $CO_2$ Hops extracts are contemplated for use in the products of the present invention. In a preferred method, the Hops extract used in the products of the present invention is produced by a two-step extraction process. The first step produces what is called herein a "total extract" wherein the extract comprises essential oils and hop acids. The second step of the process produces an extract that is very low in essential oils, which is herein referred to as a "flavor-reduced extract." In one embodiment, the flavor-reduced extract comprises less than about 5% essential oils. In a preferred embodiment, the flavor-reduced extract comprises less than about 2% essential oils. Removed components include, for example, β-myrcene, trans-caryophyllene and α-humulene (see, e.g., FIGS. 2 and 3)

In one embodiment of the present invention, it is contemplated that the two-step hops extract of the present invention is produced, for example, as follows. The first step comprises extraction by $CO_2$ at, for example, about 300-350 bar and about 40-50° C. This first step produces a primary extract resembling a stiff yellow mass at ambient temperature but is liquid enough at 40-50° C. to be pumped on the top of a purification and separation column (approximately 6 meter separation length), containing a stainless steel mesh media packing material which is available commercially (e.g., from Dollinger Filtration, Ocala, Fla.; AMCO Engineering Works, Kolkata, West Bengal, India; Fluid Air Filter Systems, Naperville, Ill.). The column extracts/strips out the more soluble essential oil components by $CO_2$-extraction as well as separating out more of the particulate contaminants by physical extraction. The intermediate hop extract (from the first step) is referred to as the "total extract," containing the complete lipophilic fraction (hop acids and essential oils).

The second step of the extraction process is performed at, for example, about 180-250 bar and about 45-60° C. It uses a lower gas density thereby resulting in an accordingly lower dissolving capacity and higher selectivity. This second extraction step helps reduce the essential oil component of the extract to less than about 2% by weight. The final extract produced by the second step is referred to as the "flavor-reduced" extract. The two-step process ensures the greatest amount of essential oils is removed from the extract efficiently.

The flavor reduced extract used in the present invention is standardized to, e.g., about 50% total hop acids by MCT (medium chain triglycerides) oil addition, for example. The addition of this oil also makes the product more liquid and easier to handle. Although the present invention is not limited by the addition of other ingredients to the flavor-reduced Hops extract of the present invention, in a preferred embodiment, no other excipients or additives are combined with the extract before its inclusion in the deodorant and body care products of the present invention. Although the hops extract used in the products of the present invention are not limited by final concentrations of hops components in the extract, in a preferred embodiment, the final extraction product comprises about 65% hop extractives and about 35% MCT oil however, in one embodiment the concentration of MCT oil may be between 1-80%. This flavor reduced extract (i.e., removing most of the essential oils contained in the hops extract) overcomes the disadvantage of regular hops $CO_2$ extracts, which have a distinct odor of beer, which is not desirable in cosmetic formulations.

Although the present invention is not limited by the nature of the body care product that comprises the $CO_2$ hops extract of the present invention, the following non-limiting products are contemplated by the present invention: underarm deodorant, body deodorant, body creams and lotions, oral care compositions, hair care products, shaving products, etc.

In a preferred embodiment, the present invention contemplates a deodorant or body care product comprising a $CO_2$-extract of hops having bacteriostatic and/or bactericidal properties. In this embodiment, the deodorant or body care product of the present invention comprises a $CO_2$ extract of hops at a concentration of between approximately 0.001% and 5.0% by weight. In another embodiment, the deodorant or body care product of the present invention comprises a $CO_2$ extract of hops at a concentration of between approximately 0.05% and 1.0% by weight. In a most preferred embodiment, the deodorant or body care product of the present invention comprises a $CO_2$ extract of hops at a concentration of between approximately 0.1% and 0.5% by weight.

In another embodiment, the body care and deodorant products of the present invention comprises an antioxidant compound. In a preferred embodiment, the antioxidant compound is selected for one or more of tocopherol and its derivatives of about 0.001-0.5%, butyl hydroxyanisole (BHA) of about 0.0075-0.1%, butyl hydroxytoluene (BHT) of about 0.005-0.02%, erythorbic acid of about 0.05-1.0%, propyl gallate of about 0.01-1.0%, sodium erythorbate of about 0.05-1.0%, tertiary butyl hydroquinone (TBHQ) of about 0.005-0.1%, rosemary extract of about 0.02-0.4% and, more preferably, ascorbic acid and salts thereof or about 0.01-0.1%.

In another embodiment, the body care and deodorant products of the present invention comprises additional deodorizing compounds. In one embodiment, the compounds are selected from a group comprising various metal salts of an unsaturated carboxylic acid. In a preferred embodiment the additional deodorizing compound is zinc ricinoleate. In another embodiment, the additional deodorizing compounds are also selected from a group consisting of glyceryl laurate, caprylic capric triglyceride and lemongrass oil, all of about 0.1-4.0%.

In another embodiment, the body care and deodorant products of the present invention additionally comprises ingredients to improve the skin feel of the products of the present invention. For example, the present invention may comprise one or more of propylene glycol of about 5-80%, water of about 5-40%, sodium stearate of about 0.5-10%, aloe extract or juice of about 0.5-10%, witch hazel (also known as witch hazel water) of about 1-10% and chamomile aqueous extract of about 1-20%.

In a preferred embodiment, the body care and deodorant products are preferably made up of one or more of the following: about 35% to about 70% by weight of a polyhydric alcohol; about 1.25% to about 6.5% by weight of a polyamine clarifier; about 1.25% to about 8.0% by weight of a $C_{14-22}$ fatty acid salt; water in an amount less than about 40% by weight; about 0.5% to 4.0% of an ester of glycerin and a $C_{8-18}$ fatty acid; and, optionally one or more ingredients selected from the group consisting of an herbal extract with anti-inflammatory or soothing properties; silicone copolyol; zinc pyridinethiol oxide; fragrance and color.

In a preferred embodiment, the herbal extract of the present invention may be selected from one or more of a group consisting of extracts of the following plants: *Aloe barbadensis* and other *Aloe* species, *Boswellia serrata*, *Calendula officinalis*, *Camellia sinensis*, *Curcuma longa*, *Curcuma xanthorrhiza*, *Glycyrrhiza glabra*, *Glycyrrhiza uralensis*, *Hamamelis virginiana*, *Mangifera indica*, *Matricaria recutita*, *Melissa officinalis*, *Rosmarinus officinalis*, *Scutellaria lateriflora*, *Scutellaria baicalensis*, *Thymus vulgaris*, *Thymus zygis*, *Uncaria tomentosa*, *Zingiber officinalis*.

In one embodiment, the polyhydric alcohol of the present invention is selected from the group consisting of organic compounds which contain about 2 to about 6 carbon atoms and about 2 to about 6 hydroxy groups. In a preferred embodiment, the polyhydric alcohol is selected from the group consisting of ethylene glycol, propylene glycol, 1,3-propanediol, trimethylene glycol, butylene glycol, diethylene glycol, dipropylene glycol, glycerin, sorbitol, xylitol and mixtures thereof. In a more preferred embodiment, the polyhydric alcohol is propylene glycol or dipropylene glycol or a mixture thereof. The concentration of the polyhydric alcohol in the compositions of the present invention range from about 35% to about 70% by weight.

In another embodiment, the body care and deodorant products of the present invention, the polyamine is a homopolymer of units of structural formula (1),

(1)

where R1 is hydrogen or a $C_{1-3}$ alkyl group and n is an integer from 2-6, and the number of repeating units of structural formula (1) is, on average about 1450 to about 1550. Non-limiting examples of polyamines suitable for use in the present invention are described in U.S. Pat. No. 5,714,447 issued to Jones, et al., on Feb. 3, 1998 and U.S. Pat. No. 6,001,342 issued to Forestier, et al., on Dec. 14, 1999, both of which are incorporated herein by reference.

In another embodiment, the body care and deodorant products of the present invention comprise a clarifier-surfactant selected from the group consisting of pentadoxynol-200, tetra (hydroxypropyl)diamine, 2-amino-2-methylpropanol, 2-amino-2-hydroxymethyl-1,3-propanediol, poly($C_{2-4}$ alkylene) glycol ethers of $C_{12-22}$ fatty alcohols in which the polyalkylene glycol portion contains from about 10 to about 100 alkyleneoxide repeating units. In a preferred embodiment, the clarifier-surfactant is selected from the group consisting of laureth-10, laureth-20, laureth-30, laureth-40, PEG-10 Myristyl Ether, steareth-10, steareth-20, steareth-40, steareth-100, PEG-50 Stearyl Ether, steareth-100 and beheneth-20 and mixtures thereof. In a more preferred embodiment, the clarifier-surfactant is polyoxyethylene 3-pentadecyl phenyl ether. The concentration of the clarifier-surfactant in the compositions of the present invention is about 2.0% to about 3.5% by weight.

In another embodiment, the body care and deodorant products of the present invention comprise a fatty acid salt selected from the group consisting of alkali metal, alkaline earth metal, aluminum, and amine salts of $C_{14-22}$ fatty acids. In a preferred embodiment, the said $C_{14-22}$ fatty acid salt is selected from the group consisting of salts of myristic, palmitic, stearic, behenic, oleic, linoleic, and linolenic acids and mixtures thereof. In a more preferred embodiment, the $C_{14-22}$ fatty acid salt is selected from the group consisting of sodium stearate, potassium stearate, aluminum monostearate, sodium oleate, sodium palmitate, sodium behenate, diethylamine stearate, triethylamine stearate, and triethylamine oleate, and mixtures thereof. The concentration of the $C_{14-22}$ fatty acid salt is about 2.2% to about 7.0% by weight.

In another embodiment, the body care and deodorant products of the present invention comprise an ester of glycerin and a fatty acid selected from the group consisting of $C_{8-18}$ fatty acids. In a preferred embodiment, the $C_{8-18}$ fatty acid is selected from the group consisting of caprylic, capric, lauric, myristic, palmitic, stearic, oleic, linoleic, and linolenic acids and mixtures thereof. The concentration of the $C_{8-18}$ fatty acid ester in the compositions of the present invention is about 0.5% to about 4.0% by weight.

The invention will now be described below in the context of specific non-limiting examples. One skilled in the art will realize that variations of the present invention that differ somewhat from the examples given may be practiced without deviating from the teachings of the present invention.

EXEMPLIFICATION

Example 1

Preparation of the Extract

For this exemplary extraction procedure, the cones of the hop plant (*Humulus lupulus*) were harvested and dried. There are a big number of hop varieties with different aromas and acid compositions, which can be used to prepare a supercritical $CO_2$ extract. The present invention is not limited by the type or types of hops cones used. For the present extraction, the Hallertauer magnum variety was used. This variety is cultivated in Germany and is high in hop acids and readily available if needed. After harvesting and drying the hop cones they were immediately milled and pelletized to reduce the surface area (hops cones are very sensitive to oxidation/polymerization due to their big surface). The pellets were sealed in airtight containers and stored at or below 0° C. before supercritical extraction.

The extract used in the present invention was made in a two-step extraction process. The primary hop extract (from the first step) is referred to as a "total extract," containing the complete lipophilic fraction (essential oil and hop acids). The first step comprises extraction by $CO_2$ at approximately 300-350 bar and approximately 40-50° C. This primary extract was a stiff yellow mass at ambient temperature but liquid enough at 40-50° C. to be pumped on the top of a column (6 meter separation length, containing stainless steel mesh packing material, as described in detail, supra) that extracts/strips out the more soluble essential oil components again by $CO_2$-extraction.

In this step of the extraction process, the extraction performed was at approximately 180-150 bar and approximately 45-60° C. This step used a lower gas density thereby resulting in an accordingly lower dissolving capacity and higher selectivity. This second extraction step typically produced less than about 2% essential oil in the final extraction product. The final extraction product is referred to as the "flavor-reduced" extract.

The "flavor-reduced" extract used in the present invention is standardized for about 50% total hop acids by MCT (medium chain triglycerides) oil addition. The addition of this oil also made the product more liquid and easier to handle. In this example no other excipients or additives were combined with the extract. The final extraction product was composed of about 65% hop extractives and about 35% MCT (medium chain triglycerides) oil. This flavor reduced extract (removing the essential oils contained in the hops extract) overcomes the disadvantage of regular hops $CO_2$ extracts, which have a distinct odor of beer, which is not desirable in cosmetic formulations. This "flavor-reduced" extract was used in the following exemplifications.

Example 2

Comparison of the Flavor-Reduced Supercritical Hops Extracts to Commercially Available Hops $CO_2$-Extracts The flavor-reduced hops extract used in the present invention was compared to three other commercial hops $CO_2$ extracts (two regular $CO_2$ extracts, and a β-acid-rich extract) using infrared spectroscopy (FT-IR), gas-chromatography with a mass-spectrometric detection (GC-MS), and high-performance liquid chromatography with photodiode array detection (HPLC-DAD). The main differences between the flavor-reduced extract and commercially available hops $CO_2$ extracts, were 1) the absence of essential oil (in particular β-myrcene, trans-caryophyllene and α-humulene) in the flavor-reduced extract, 2) a lower percentage of hops acids in the flavor-reduced extract and 3) the presence of caprylic/capric triglyceride in the flavor-reduced extract of the present invention. All analysis equipment was operated as per manufacturers directions under the specific parameters described below.

IR analysis (Perkin-Elmer Model Spectrum 100; see, FIG. 1): The IR spectrum of the flavor-reduced hops extract was very distinct from the prior art hops $CO_2$ extracts. In particular, the flavor-reduced extract of the present invention differs by the intensity of the OH band at 3500 cm$^{-1}$, by the presence of an intense carbonyl band from the caprylic/capric triglyceride ester function (1720 cm$^{-1}$), and by some very distinct differences in the C—O—H bending and the C—H (isoprenyl groups) bending band region between 1300 and 1500 cm$^{-1}$ and the C—O stretching band region (1100-1250 cm$^{-1}$).

Figure 2:
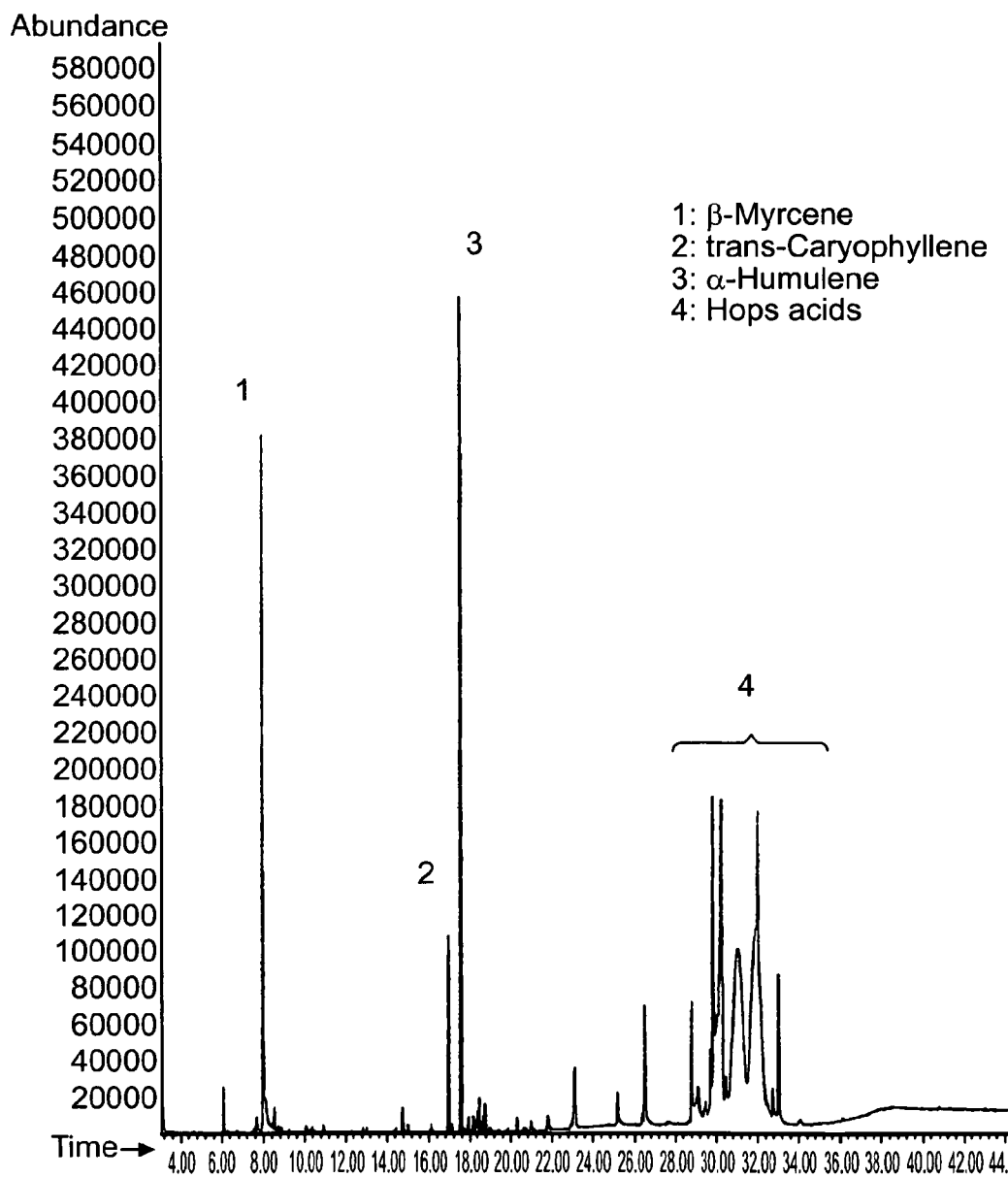
FIG. 2 shows GC-MS analysis (Agilent Technologies Model 5890N) of a representative analysis of the prior art commercially produced $CO_2$ hops extracts.
Figure 3:
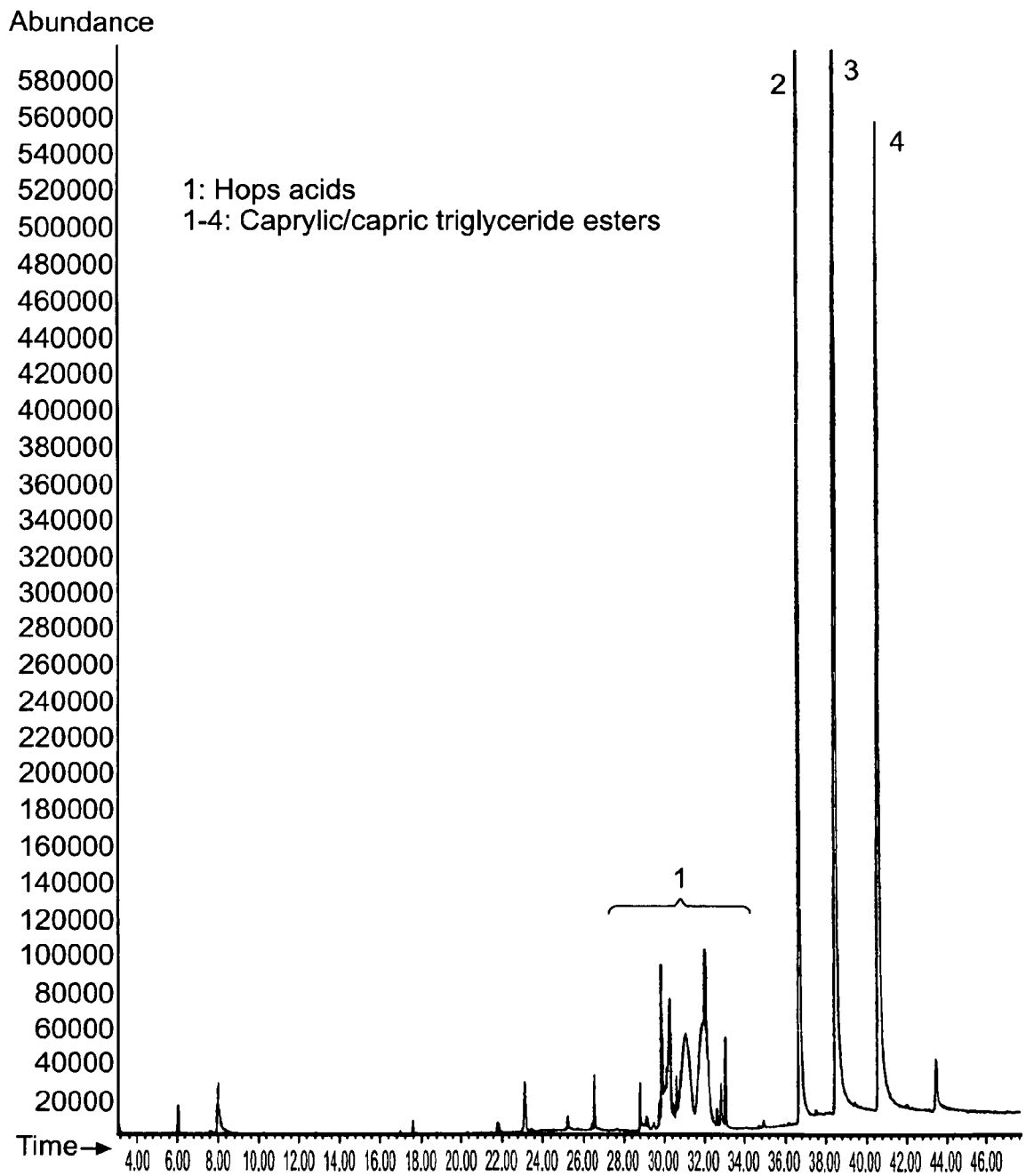
FIG. 3 shows GC-MS analysis (Agilent Technologies Model 5890N) of the flavor-reduced hops $CO_2$ extract.

GC-MS analysis (Agilent Technologies Model 5890N): The GC-MS analysis showed a clear distinction between the flavor-reduced extract of the present invention and the prior art hops $CO_2$ extracts. The flavor components (β-myrcene, trans-caryophyllene and α-humulene as the most prominent) are the most intense peaks in the prior art $CO_2$ extracts (FIG. 2). The flavor-reduced hops $CO_2$ extract lacks all these components, but shows some intense peaks towards the end of the chromatogram due to the presence of capric/caprylic triglyceride (FIG. 3), which is added into the extract to reduce the tackiness (easier to formulate) and to adjust the contents of the hops acids to the desired level.

Figure 4:
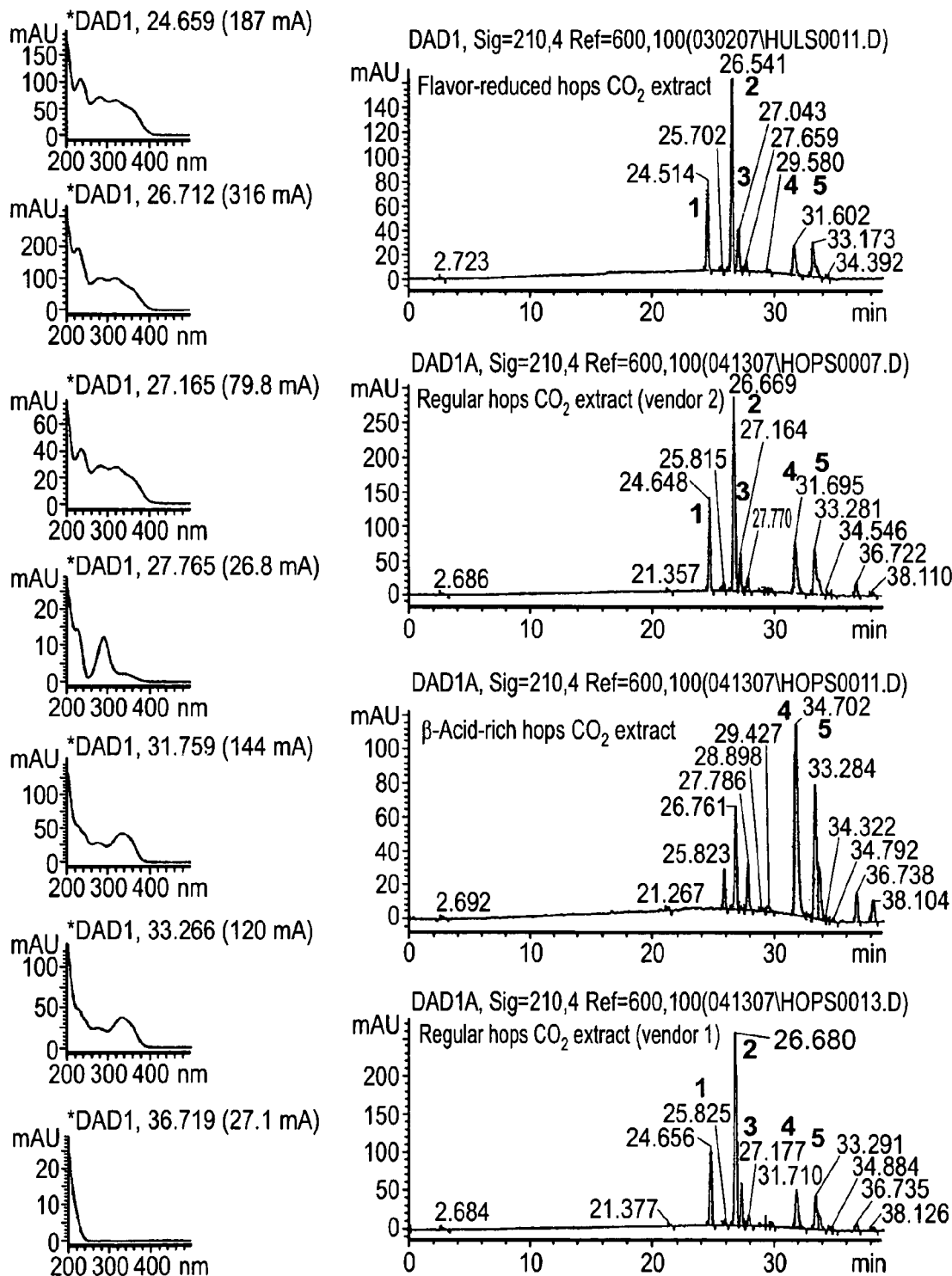
FIG. 4 shows an HPLC-DAD analysis (Agilent Technologies 1100 system): HPLC-DAD analysis at 210 nm and 314 nm showed differences in the chromatographic patterns of the prior art $CO_2$ extracts and the flavor-reduced extract of the present invention.

HPLC-DAD analysis (Agilent Technologies 1100 system): HPLC-DAD analysis at 210 nm (FIG. 4) and 314 nm showed differences in the chromatographic patterns of the prior art $CO_2$ extracts and the flavor-reduced extract of the present invention. A commercial extract with reduced α-acid fraction did, as expected, contain a lesser amount of α-acids in comparison, and a larger amount of the more lipophilic β-acids. The quantitative analysis of the hops acids gave a content of about 75% hops acids in the prior art $CO_2$ extracts, compared to 51.3% obtained for the flavor-reduced hops $CO_2$ extract of the present invention. A lesser amount was obtained for the β-acid-rich hops $CO_2$ extract.

Methods

GC-MS: The following conditions to analyze all samples:

Column: Agilent HP-5, 30 m×0.25 m×0.25μ film thickness; Inlet temperature: 25° C., pressure 7.63 psi (pound per square inch) at 50° C., split ratio 50:1; Helium carrier gas, column flow (constant) 1.0 ml/min; Temperature program: 50° C., hold 2 min; ramp 7° C./min to 300° C., hold 10 min.; MS transfer line temperature: 280° C.; MS source temperature: 230° C.; MS quad temp: 150° C.; Scan: 50-500 amu (atomic mass unit).

HPLC-UV: The following conditions to analyze all standards and samples:

Column: Zorbax Eclipse XDB C-18 250×4.6 mm i.d. (inner diameter) with Zorbax C-18 Guard Column;

| Mobile Phase: MeCN (0.005% TFA)-H$_2$O (0.005% TFA) | | |
|---|---|---|
| 0 min. | 45 | 55 |
| 3 min. | 45 | 55 |
| 32 min. | 95 | 5 |
| 37 min. | 95 | 5 |
| 39 min. | 45 | 55 |

Section 1.01 Flow Rate: 1.0 ml/min; Column temperature: 35° C.; Detector wavelength 314 nm, bw (bandwidth in nm) 16 (reference 500 nm, bw 100); Run time: 39 min.; Post time: 7 min.

TABLE 1

Results of minimum inhibitory concentration broth microdilution test vs. *Corynebacterium xerosis* ATCC #373:

| Active material | MIC vs. *C. xerosis* ATCC #373 in micrograms/ml |
|---|---|
| *H. lupulus* methylene chloride extract, #SG-X-31A | 125 |
| *H. lupulus* hexane extract, #SG-X-31B | 15.6 |
| *H. lupulus* petroleum ether extract, #SG-X-31C | 15.6 |
| *H. lupulus* alcohol extract, #SG-X-31D | 125 |
| *H. lupulus* methanol extract, #SG-X-31E | 62.5 |
| *H. lupulus* acetone extract, #SG-X-31F | 125 |
| Flavor Reduced Hops CO$_2$ extract | 3.9 |

The antimicrobial activity of the supercritical hops extract was further evaluated in an assay involving underarm swabs of seven volunteers and in zone of inhibition assays against skin bacteria (*Corynebacterium xerosis, Staphylococcus aureus* and *S. epidermidis*) known to be involved in the formation of malodorous compounds after sweating.

Results: The supercritical hops extract was able to inhibit the growth of bacteria in 5 subjects out of 7 at a concentration of 31.25 μg/ml, or lower.

TABLE 2

Minimum inhibitory concentration of assorted extracts/oils vs. axillary swab cultures.

|  | culture #1 | culture #2 | culture #3 | culture #4 | culture #5 | culture #6 | culture #7 |
|---|---|---|---|---|---|---|---|
| Ingredient 1 | 250 | 250 | 250 | 250 | 250 | >250 | >250 |
| Ingredient 2 | 125 | 250 | 250 | 250 | 31.25 or 15.6 | >250 | >250 |
| Ingredient 3 | >250 | >250 | >250 | >250 | >250 | >250 | >250 |
| Ingredient 4 | >250 | >250 | >250 | >250 | >250 | >250 | >250 |
| hops CO$_2$ extract | 15.6 (or less) | 15.6 (or less) | 31.25 | 15.6 (or less) | 15.6 (or less) | >250 | >250 |
| Ingredient 6 | 31.25 | 31.25 | 62.5 | >250 or 31.25 | 31.25 | >250 | >250 |
| Ingredient 7 | >250 | >250 | >250 | >250 | >250 | >250 | >250 |
| Ingredient 8 | >250 | 250 | 250 | >250 | 125 | 250 or >250 | >250 |
| Ingredient 9 | >250 | >250 | >250 | >250 | 250 | >250 | >250 |
| Ingredient 10 | >250 | >250 | >250 | >250 | >250 | >250 | >250 |

MIC in micrograms/mL, mode value from six reps (concentrations tested: 250-125-62.5-31.25-15.6 micrograms/mL)

Notes:
1) Cultures # 6 and 7 showed high levels of bacteria in the cultures treated with the hops extract of the present invention because of the presence of gram negative bacteria in the samples. Gram negative bacteria are generally not odor causing. Follow-up studies showed odor causing gram positive bacteria were eliminated in all of the samples (# 1-7) treated with the hops CO$_2$ extract of the present invention.
2) Ingredients 1-10 were extracts of other various non-hops plants.

Sample preparation: Approximately 15 mg of hops CO$_2$ extract were weighed into a 10 mL volumetric flask. The flask was filled with HPLC grade alcohol to the mark and the CO$_2$ extract dissolved by sonicating the flasks for 5 minutes. The solution was filtered using 0.2 μm polypropylene filters and a volume of 2 μl was injected into the HPLC.

Example 3

Results of Broth Microdilution Test vs. *Corynebacterium xerosis* (ATCC #373) and of Minimum Inhibitory Concentration (MIC) of Axillary Swab Samples In-house antimicrobial testing revealed that the CO$_2$ extract did have superior antimicrobial activities than extracts obtained with different organic solvents (hexane, petroleum ether, acetone, ethanol, methanol or methylene chloride).

Methods

Armpit swab MIC: The hops CO$_2$ extract was tested on a culture of an armpit swab from seven volunteers in order to confirm that the extract was able to reduce the population of bacteria on different individuals. Seven volunteers used sterile swabs to obtain samples of their own axillary bacteria, twelve hours post-washing. Swabs were incubated in tryptic soy broth (TSB) overnight at 37° C. Each culture was diluted with sterile TSB to match a McFarland 0.5 turbidity standard, and then further diluted to give a concentration of approximately $1.5 \times 10^6$ cfu per mL. The MIC was performed in 96 well plates. The final concentrations were 250, 125, 62.5, 31.25 and 15.6 ug/mL with a final inoculum concentration of about $1.5 \times 10^5$ cfu per well. Triclosan was used as positive control, while the negative control consisted of DMSO and 60% EtOH. Plates were incubated under aerobic conditions at 37° C. until turbidity was evident in the growth control well. The MIC was taken as the lowest concentration at which growth was inhibited, as viewed with the unaided eye.

Example 4

Results of Zone of Inhibition Testing

Zone of inhibition testing: The test organism was grown on a nutrient agar medium (Tryptic Soy or other appropriate nutrient agar medium) for 18-24 hours at 37° C. (or longer if fastidious). Using a sterile inoculating loop, surface growth was suspended in sterile diluent to visually match the McFarland 0.5 standard. Within 15 minutes of inoculum preparation, a sterile cotton swab was dipped into the suspension, withdrawn, and then pressed and rotated against the inside of the tube above the liquid level to remove excess fluid. The swab was streaked across the entire surface of an agar plate in three directions, rotating the plate about 60° each time to ensure thorough coverage. Finally, the swab was swept around the inside rim of the plate and discarded appropriately.

Within 15 minutes of inoculation, alcohol cleaned forceps were used to apply a 6 mm filter paper disk carrying the test material to the agar surface. If the test material was a liquid a measured volume was pipetted on to the disk. If the material was a solid it was melted, the filter paper disk was dipped into the melted material to create a uniform coating prior to application to the agar surface. Additionally, a stock solution of desired concentration may be prepared in non-active diluent and applied by volume or "dipping." If a diluent was used, it was tested as a control to ensure it had no activity of its own. Once a disk had been placed, it was not moved. Multiple disks were applied to plates, but in general not more than five per 100 mm plate or 12 per 150 mm plate were used.

After addition of the test material, the agar plates were incubated for 24 hours at 37° C. though conditions may be altered to meet the requirements of more fastidious bacteria.

Materials which were active against the test bacterium displayed clear zones of growth inhibition surrounding the disk. The diameter of the entire zone, including the disk, was measured in millimeters by placing a measuring device against the bottom of the inverted Petri dish. Tests were performed at least in triplicate and a mean zone of inhibition was calculated.

TABLE 3

Results (in diameter [mm] of zone of inhibition) from repetitive (n = 3) disk diffusion assays:

| | Hops (0.15% in DMSO) | Hops (0.2% in DMSO) | DMSO |
|---|---|---|---|
| S. aureus | 11 | 11 | no activity |
| S. epidermidis | 9 | 9 | no activity |
| C. xerosis | 12 | 15 | no activity |

We claim:

1. A body care product comprising a flavor-reduced hops extract wherein said hops extract is produced by a two-step supercritical $CO_2$ extraction process, said extract comprising alpha and beta hops acids and comprising less than 2% hops essential oils, wherein said body care product is effective in preventing or lessening body odor, and wherein said hops extract is at a concentration of between 0.001-5.0 percent w/w.

2. The body care product of claim 1, wherein said body care product is a body deodorant or an underarm deodorant.

3. The body care product of claim 1, wherein said two-step supercritical $CO_2$ extraction process comprises a first step, said first step comprising the extraction of dried hops by $CO_2$ at between approximately 300-350 bar and at between approximately 40-50° C. to produce an intermediate extract and a second step comprising the extraction of the intermediate extract by $CO_2$ at approximately 180-250 bar and 45-60° C. to produce a final extract.

4. The body care product of claim 1, wherein said hops extract is at a concentration of between 0.05-1.0 percent w/w.

5. The body care product of claim 1, wherein said hops extract is at a concentration of between 0.1-0.5 percent w/w.

6. The deodorant of claim 2, wherein said deodorant additionally comprises one or more thickening agents, one or more soothing agents, one or more additional deodorancy agents, one or more antioxidants and, optionally, one or more fragrances.

7. The deodorant of claim 6, wherein said fragrance additionally comprises a carrier, said carrier comprising silica shells.

8. The deodorant of claim 6, wherein said thickening agents are selected from one or more of propylene glycol and sodium stearate and wherein said thickening agents are combined with water.

9. The deodorant of claim 6, wherein said soothing agents are selected from one or more of an extract of aloe vera, chamomile extract and witch hazel.

10. The deodorant of claim 6, wherein said deodorancy agents may additionally comprise one or more of metal salts of an unsaturated hydroxy carboxylic acid, capric/caprylic triglyceride, lemongrass oil and glyceryl laurate.

11. The deodorant of claim 10, wherein the metal salt of an unsaturated hydroxy carboxylic acid is zinc ricinoleate.

12. The deodorant of claim 6, wherein said antioxidant is selected from one or more of a group consisting of ascorbic acid and salts thereof, tocopherol and its derivatives, butyl hydroxyanisole (BHA), butyl hydroxytoluene (BHT), erythorbic acid, propyl gallate, sodium erythorbate, tertiary butyl hydroquinone (TBHQ) and rosemary.

13. The deodorant of claim 2, wherein said deodorant also comprises an herbal extract.

14. The deodorant of claim 13, wherein said herbal extract selected from one or more extracts of the following plants: *Aloe barbadensis* and other *Aloe* species, *Boswellia serrata*, *Calendula officinalis*, *Camellia sinensis*, *Curcuma longa*, *Curcuma xanthorrhiza*, *Glycyrrhiza glabra*, *Glycyrrhiza uralensis*, *Hamamelis virginiana*, *Mangifera indica*, *Matricaria recutita*, *Melissa officinalis*, *Rosmarinus officinalis*, *Scutellaria lateriflora*, *Scutellaria baicalensis*, *Thymus vulgaris*, *Thymus zygis*, *Uncaria tomentosa* and *Zingiber officinalis*.

15. The body care product of claim 1, wherein said body care product additionally comprises one or more of propylene glycol, water, sodium stearate, zinc ricinoleate or glyceryl laurate.

16. The body care product of claim 1, wherein said hops extract also comprises one or more of caprylic or capric triglyceride.

17. The body care product of claim 1, wherein said hops extract is extracted from one or more of the Asian Hop *Humulus japonicus* (syn. *H. scandens*); the Yunnan Hop *Humulus yunnanensis*; and the Common Hop *Humulus lupulus*.

* * * * *